US008846612B2

(12) United States Patent
Aprikian et al.

(10) Patent No.: US 8,846,612 B2
(45) Date of Patent: Sep. 30, 2014

(54) PROMOTION OF HEALTHY CATCH-UP GROWTH (75) Inventors: Olivier Aprikian, Dublin, OH (US); Florence Blancher, Morges (CH); Catherine Mace, Lausanne (CH); Yassaman Shahkhalili, La Tour de Peitz (CH)

(73) Assignee: Nestec S.A., Vevey (CH)

( * ) Notice: Subject to any disclaimer, the term of this patent is extended or adjusted under 35 U.S.C. 154(b) by 11 days.

(21) Appl. No.: 13/260,817

(22) PCT Filed: Mar. 26, 2010

(86) PCT No.: PCT/EP2010/054032
§ 371 (c)(1),
(2), (4) Date: Sep. 28, 2011

(87) PCT Pub. No.: WO2010/112430
PCT Pub. Date: Oct. 7, 2010

(65) Prior Publication Data
US 2012/0021977 A1    Jan. 26, 2012

(30) Foreign Application Priority Data

Apr. 3, 2009  (EP) .................................... 09157244

(51) Int. Cl.
| A61K 38/00 | (2006.01) |
| A61P 3/02 | (2006.01) |
| A61K 38/17 | (2006.01) |
| A61K 31/405 | (2006.01) |
| A61K 35/20 | (2006.01) |
| A61K 31/198 | (2006.01) |
| A23L 1/305 | (2006.01) |
| A61K 31/4172 | (2006.01) |
| A61K 38/01 | (2006.01) |

(52) U.S. Cl.
CPC .......... *A61K 38/1709* (2013.01); *A61K 31/405* (2013.01); *A61K 35/20* (2013.01); *A61K 31/198* (2013.01); *A23L 1/3056* (2013.01); *A61K 31/4172* (2013.01); *A61K 38/018* (2013.01); *A23V 2002/00* (2013.01)
USPC ............................................ 514/5.6; 514/5.7

(58) Field of Classification Search
CPC ............ A61K 2300/00; A61K 31/198; A61K 31/405; A61K 31/4172; A61K 38/018; A61K 38/1709; A61K 35/20; A23V 2002/00; A23V 2200/328; A23V 2250/54246; A23L 1/3056
See application file for complete search history.

(56) References Cited

U.S. PATENT DOCUMENTS 6,787,158 B1   9/2004  Erdmann et al.

FOREIGN PATENT DOCUMENTS

| CN | 1215311 | 4/1999 |
| CN | 1368853 | 9/2002 |
| CN | 1860131 | 11/2006 |
| CN | 101212911 A | 7/2008 |
| CN | 101378669 | 3/2009 |
| EP | 0880902 | 12/1998 |
| EP | 932437 A1 * | 6/2008 ................ A23L 1/29 |
| WO | 02083164 | 10/2002 |
| WO | 2007088160 | 8/2007 |

OTHER PUBLICATIONS

Bindels et al. Specialised feed: nutrition of low birth weight infants, Current Paediatrics, vol. 3, p. 42-47, 1993.*
Dulloo et al. The thrifty 'catch-up fat' phenotype: its impact on insulin sensitivity during growth trajectories to obesity and metabolic syndrome, International Journal of Obesity, vol. 30, S23-S35.*
MayoClinic-Diabetes risk factors, copyright 1998-2014-accessed Feb. 21, 2014).*
Harvard school of public health-accessed Feb. 21, 2014.*
Gillies et al. (BMJ, doi:10.1136/bmj.39063.689375.55, published Jan. 19, 2007).*
Web MD-Metformin oral-copyright 1998-2014, accessed Feb. 21, 2014.*
Committee on Nutrition, "Nutritional Needs of Low-Birth Weight Infants", Pediatrics, May 1985, pp. 976-986, vol. 75, No. 5.
Bindels J G et al: "Specialised feeds: nutrition of low birth weight infants," Current Paediatrics, Churchill Livingstone, Edinburgh, GB, vol. 3, No. 1, Mar. 1, 1993, pp. 42-47, XP022967493; ISSN: 0957-5839 [retrieved on Mar. 1, 1993), pp. 43-44.
Cianfarani et al.: "Low birth Weight and Adult Insulin Resistance: The "Catch-Up Growth" Hypothesis." Archives of Disease in Childhood-Fetal and Neonatal Edition 81, No. 1 (1999): F71-F73.
Simmons R A et al: "Intrauterine growth retardation leads to the development of type 2 diabetes in the rat," Diabetes, vol. 50, No. 10, Oct. 2001, pp. 2279-2286, XP002535619; ISSN: 0012-1797, p. 2281.
Crescenzo et al.: "A role for suppressed thermogenesis favoring catch-up fat in the pathophysiology of catch-up growth." Diabetes 52.5 (2003): 1090-1097.

(Continued)

*Primary Examiner* — James H Alstrum Acevedo
*Assistant Examiner* — Tara Martinez
(74) *Attorney, Agent, or Firm* — K&L Gates LLP (57) ABSTRACT The use of a protein source comprising bovine casein proteins for the preparation of a nutrional composition for administration to an infant, young child or adult during or after a period of catch-up growth or weight recovery, following a period of growth restriction or weight lost, so as improve growth at early age and/or to reduce the risk of development of insulin resistance and/or Type 2 diabetes later in the life of the infant, young child or adult.

14 Claims, 5 Drawing Sheets

(56) References Cited

OTHER PUBLICATIONS

Levy-Marchal et al.: "Long-term metabolic consequences of being born small for gestational age." Pediatric diabetes 5.3; Sep. 27, 2004: 147-153.

Kempley et al: "Which milk for the sick preterm infant?", Current Paediatrics, Churchill Livingstone, Edinburgh, GB LNKD-DOI: 10.1016/J.CUPE.2005.06.005, vol. 15, No. 5, Oct. 1, 2005, pp. 390-399, XP005086694; ISSN: 0957-5839, p. 394; tables 1,2.

Acta Paediatrica, "WHO Child Growth Standards," vol. 95, Apr. 2006, Supplement 450.

Dullo, A G: "Regulation of fat storage via suppressed thermogenesis: a thrifty phenotype that predisposes individuals with catch-up growth to insulin resistance and obesity." Hormone Research in Paediatrics 65, No. 3; Apr. 10, 2006: 90-97.

Robert C D et al: "Metabolic effects of different protein intakes after short term undernutrition in artificially reared infant rats," Early Human Development, Shannon, IR LNKD-DOI: 10.1016/J.EARLHUMDEV.2008.06. 009, vol. 85, No. 1, Jan. 1, 2009, pp. 41-49, XP025817051; ISSN: 0378-3782 [retrieved on Jul. 23, 2008], p. 46, table 1.

PCT International Search Report for Application No. PCT/EP2010/054032 with a Mailing Date of May 31, 2010. 4 Pages.

\* cited by examiner

Figure 1 :
*: P<0.02 (casein vs whey & whey micelles)

\* p<0.001 between non IUGR and IUGR groups (ANOVA)

a : P< 0.0001 casein diet vs Whey diet
b : P= 0.07 casein diet vs Whey diet

Figure 4

*: p≤0.05 for 2-h glucose AUC between IUGR casein and IUGR whey groups (t- test)

Figure 5

*: p≤0.05 between IUGR casein and IUGR whey groups (t- test)

PROMOTION OF HEALTHY CATCH-UP GROWTH

CROSS REFERENCE TO RELATED APPLICATIONS

The present application is a National Stage of International Application No. PCT/EP2010/054032, filed on Mar. 26, 2010, which claims priority to European Patent Application No. 09157244.6, filed on Apr. 3, 2009, the entire contents of which are being incorporated herein by reference.

BACKGROUND OF THE INVENTION

This invention relates to the use of certain proteins to improve healthy growth and reduce the risk of development of insulin resistance as a consequence of uncontrolled (unhealthy) catch-up growth in infants and children and weight recovery in adults.

It has been recognized for many years that the growth pattern of young mammals who suffer stress whether as a result of physical illness or injury or psychological trauma is often interrupted. If the young mammal makes a swift recovery and adequate nutrition is available, it may then compensate for the growth which should have taken place during the period of stress and this sudden spurt of growth is known as "catch up growth". However, this does not always happen. For example, the young mammal may suffer from anorexia both during the illness or trauma and in its immediate aftermath and food intake may therefore be limited. In severe cases it may be that the animal never attains the physical stature that it would have reached had the stress not been suffered.

This phenomenon may be seen in young mammals including humans from infancy throughout the period in their lives during which they are still growing. It may be particularly noticeable in the case of young mammals born prematurely as well as those which do not achieve normal growth patterns before birth for whatever reason. In the case of human infants such individuals may be described as subject to intra-uterine growth restriction ("IUGR").

Although it is desirable to ensure that reduced growth during periods of physical or mental stress is compensated, it is also important to reduce the risk of later development of metabolic disease as a consequence of unhealthy catch up growth. Without being bound by the theory, it is also believed that catch up growth should not be excessive as there are indications that periods of very rapid and/or very extensive catch up growth particularly during infancy may be linked with a risk of future obesity. It is also important that catch up growth is not accompanied by excessive fat deposition and hyperinsulinemia, as these features of catch-up growth may be linked with a risk of future obesity and diabetes.

Indeed, there is increasing evidence to suggest that people who had low birth weight or who were stunted during infancy or childhood, but who subsequently showed catch-up growth, have higher susceptibility for central obesity, type 2 diabetes and cardiovascular diseases later in life (Cianfarani S, Germani D, Branca F: Low birth weight and adult insulin resistance: the 'catch-up growth' hypothesis. Arch Dis Child Fetal Neonatal Ed 81:F71-3 (1999), Levy-Marchal C, Jaquet D, Czernichow P: Long-term metabolic consequences of being born small for gestational age. Semin Neonatol 9:67-74 (2002)). Recently, it has been suggested that the phase of catch-up growth may correspond to a state of hyperinsulinaemia concomitant to a disproportionately faster rate of recovering body fat than that of lean tissue (Dulloo A G. Regulation of fat storage via suppressed thermogenesis: a thrifty phenotype that predisposes individuals with catch-up growth to insulin resistance and obesity. Hormone Research 65, Suppl 3: 90-7 (2006)).

Insulin resistance occurs when the body fails to respond properly to the action of insulin produced by the pancreas. It occurs most frequently in adults, but is being noted increasingly in adolescents and younger children as well. The body attempts to overcome this resistance by secreting more insulin from the pancreas. The development of Type 2, or non-insulin dependent, diabetes occurs when the pancreas fails to sustain this increased insulin secretion.

This dispropostional rate of recovery of body fat relative to lean mass also occurs in adult during phase of "weight recovery" following weight lost due to illness, dieting, etc.

There is, therefore, clearly a need for an intervention specifically designed to address the nutritional needs of infants and young children undergoing periods of catch-up growth whilst reducing their risk of developing insulin resistance or Type 2 diabetes or obesity later in life.

Similarly there is a need for interventions specifically designed to address the nutritional needs of subject, of young age or adults, undergoing weight recovery whilst reducing their risk of developing insulin resistance or Type 2 diabetes or obesity later in life.

SUMMARY OF THE INVENTION

Using a rat model of semistarvation-refeeding and intra-uterine growth restriction ("IUGR"), the present inventors have surprisingly discovered that the glucose intolerance and hyperinsulinaemia which often characterises periods of accelerated or catch-up growth and which has been linked with an increased susceptibility to the development of insulin resistance and ultimately Type 2 diabetes later in life can be improved by feeding a specific type of protein during or after periods of catch-up growth or weight recovery. The specific protein also improves healthy growth during fast phase of early growth.

Accordingly, the present invention provides the use of a protein source comprising bovine casein proteins for the preparation of a nutritional composition for administration to an infant or young child undergoing a period of catch-up growth following a period of growth restriction during or after the period of catch-up growth so as to reduce the risk of development of insulin resistance or Type 2 diabetes later in the life of the infant or young child and/or so as to promote healthy growth in infant and young children.

The invention extends to a method of reducing the possibility that an infant or young child undergoing a period of catch-up growth following a period of growth restriction and thereby at risk of developing insulin resistance or Type 2 diabetes later in life will develop insulin resistance or Type 2 diabetes later in life comprising feeding to the at risk infant or young child during or after the period of catch-up growth a nutritional composition including a protein source comprising bovine casein proteins.

The present invention also provides a nutritional solution based on bovine protein to reducing the risk of later diabetes development in adult during or after weight recovery following weight lost.

Preferably at least 30% by weight of the protein source is bovine casein. More preferably, bovine casein provides between 40% and 100% of the protein source.

Periods of catch-up growth may occur at any time in the life of an individual from birth to the age at which full physical stature is reached following a physical illness or injury or psychological trauma during which or as a result of which growth has been restricted. Infants who are born prematurely or who are deemed to have been subject to intra-uterine growth retardation at birth (whether or not that birth occurs prematurely by reference to the normal term of gestation of 40 weeks for humans) seem to be particularly susceptible to grow rapidly immediately after birth and to be at elevated risk of such growth involving a disproportionately high rate of fat deposition as well as hyperinsulinaemia. The present invention has particular utility in the care and nutrition of such infants. In addition the present invention has also utility for adults or Youngs during or after weight recovery.

DETAILED DESCRIPTION OF THE INVENTION

In this specification, the following expressions have the meanings assigned to them below:

"period of catch-up growth" means a rate of growth more rapid than that which would be expected in a healthy infant or young child of the same age by reference to published data including, as regards infants, the growth rates for breast fed infants set out in Acta Paediatrica, Vol 95, April 2006, Supplement 450 "WHO Child Growth Standards";

"period of growth restriction" means a rate of growth less rapid than that which would be expected in a healthy infant or young child of the same age by reference to published data including, as regards infants, the growth rates for breast fed infants set out in Acta Paediatrica, Vol 95, April 2006, Supplement 450 "WHO Child Growth Standards";

"infant" means a child under the age of 12 months;

"intra-uterine growth restrication" or IUGR means any restriction in growth in utero of an individual having regard to gestational age and potential for growth of the individual;

"protein content" means total content of proteinaceous material including free amino acids (if present);

"young child" means a child between the age of 1 and 12 years.

The term 'unhealty or uncontrolled catch-up growth" relates to excessive catch-up of body fat and excessive hyperinsulinemia that could constitute important mechanisms in the link between catch-up growth and susceptibility to later obesity and/or type 2 diabetes. On contrary "heathly catch up growth" is a controlled growth not inducing detrimental effects or reducing the risk of detrimental effects.

All percentages and ratios are by weight unless otherwise specified.

References to the energy density of the nutritional composition in a specified number of kilocalories per liter refer, in the context of powdered products, to the product after reconstitution according to the directions provided with the product.

Preferably, the nutritional composition is suitable for consumption by infants and young children. The composition may be a nutritionally complete formula such as an infant formula, a follow-on formula or a growing up milk. Alternatively for the older end of the target group of infants and young children, the composition may be a juice drink or other chilled or shelf stable beverage or a soup, or baby foods for example.

The general composition of an infant formula for use according to the invention will now be described by way of example.

The formula contains a protein source comprising bovine casein proteins. Preferably at least 30% by weight of the protein source is casein, more preferably at least 40%. The remainder of the protein source may be any protein suitable for consumption by infants provided that the minimum requirements for essential amino acid content are met. Thus, protein sources based on mixtures of bovine casein and whey proteins may be used. If whey proteins are to be used, they may be acid whey or sweet whey or mixtures thereof and may include alpha-lactalbumin and beta-lactoglobulin in whatever proportions are desired. The casein:whey ratio may lie in the range from 70:30 to 30:70. The protein source may additionally be supplemented with free amino acids if this is necessary to meet the minimum requirements for essential amino acid content. These requirements are published for example in EC Directive 2006/141/EC.

As noted above, the protein source may be a mixture of casein and whey proteins. The whey protein may be a whey protein isolate, acid whey, sweet whey or sweet whey from which the caseino-glycomacropeptide has been removed (modified sweet whey). Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. A process for removing CGMP from sweet whey is described in EP 880902.

If modified sweet whey is used as the whey protein in a mixture of 60% whey and 40% casein, the protein source may be supplemented by free tryptophan, isoleucine, histidine and phenylalanine in amounts of up to 0.34% for tryptophan, 0.92% for isoleucine, 0.19% for histidine and 2.2% for phenylalanine (in each case as a percentage by weight of total protein content). If intact sweet whey is used as the whey protein in a mixture of 60% whey and 40% casein, the protein source may be supplemented by free tryptophan, leucine, histidine and phenylalanine in amounts of up to 0.5% for tryptophan, 0.37% for leucine, 0.3% for histidine and 2.5% for phenylalanine (in each case as a percentage by weight of total protein content). The protein source may also be supplemented by amino acids rich in sulphur such as cysteine and methionine if desired.

The proteins may be intact or hydrolysed or a mixture of intact and hydrolysed proteins although intact proteins are preferred. The protein content of the infant formula may be less than 2.2 g/100 kcal, preferably between 1.6 and 2.0 g/100 kcal.

An infant formula for use according to the present invention contains a carbohydrate source. Any carbohydrate source conventionally found in infant formulas such as lactose, saccharose, maltodextrin, starch and mixtures thereof may be used although the preferred source of carbohydrates is lactose. Preferably, the carbohydrate content of the infant formula is between 9 and 14 g/100 kcal.

An infant formula for use according to the present invention contains a source of lipids. The lipid source may be any lipid or fat which is suitable for use in infant formulas. Suitable fat sources include palm olein, high oleic sunflower oil, linseed oil and high oleic safflower oil although a combination of linseed oil and high oleic safflower oil is preferred. Small amounts of oils containing high quantities of pre-formed arachidonic acid and docosahexaenoic acid such as fish oils or microbial oils. In total, the lipid content may be between 4.4 and 6 g/100 kcal. Preferably, the ratio of linoleic acid (C18:2n-6): α-linolenic acid (C18:3n-3)in the lipid source is less than 7:1, more preferably between 7:1 and 5:1.

The infant formula will also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as probiotic lactic acid bacteria, prebiotic oligosaccharides, lactoferrin, nucleotides, nucleosides, and the like.

The formula may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

If a liquid product is preferred, the homogenised mixture may be sterilised then aseptically filled into suitable containers or may be first filled into the containers and then retorted.

The invention will now be further illustrated by reference to the following examples.

EXAMPLE 1

An example of the composition of an infant formula for use according to the invention is given below:

|  | per 100 kcal | per litre |
|---|---|---|
| Nutrient |  |  |
| Energy (kcal) | 100 | 630 |
| Protein (g) (skimmed milk powder, modified sweet whey) | 1.5 | 9.45 |
| free phenylalanine (mg) | 30 | 189 |
| free isoleucine (mg) | 13.5 | 85 |
| free tryptophan (mg) | 4.9 | 30.9 |
| free histidine (mg) | 2.5 | 15.8 |
| casein:whey ratio | 40:60 | 40:60 |
| Fat (g) | 5.3 | 33.4 |
| Linoleic acid (g) | 0.7 | 4.4 |
| α-Linolenic acid (mg) | 106 | 668 |
| DHA (mg) | 11.5 | 72.5 |
| ARA (mg) | 11.5 | 72.5 |
| Linoleic acid: α-Linolenic acid | 6.5 | 6.5 |
| Lactose (g) | 11.6 | 73.1 |
| Minerals and Electrolytes |  |  |
| Na (mg) | 25 | 158 |
| K (mg) | 89 | 561 |
| Cl (mg) | 64 | 403 |
| Ca (mg) | 64 | 403 |
| P (mg) | 32 | 202 |
| Ca/P | 2.0 | 2.0 |
| Mg (mg) | 6.9 | 43.5 |
| Mn (ng) | 8.0 | 50.4 |
| Vitamins and Trace Elements |  |  |
| Vitamin A (IU) | 350 | 2205 |
| Vitamin D (IU) | 60 | 378 |
| Vitamin E (IU) | 1.2 | 7.6 |
| Vitamin K1 (µg) | 8.0 | 50.4 |
| Vitamin C (mg) | 10 | 63 |
| Vitamin B1 (mg) | 0.07 | 0.44 |
| Vitamin B2 (mg) | 0.15 | 0.95 |
| Niacin (mg) | 1.0 | 6.3 |
| Vitamin B6 (mg) | 0.075 | 0.47 |
| Folic acid (µg) | 12 | 75.6 |
| Pantomenic acid (mg) | 0.45 | 2.83 |
| Vitamin B12 (µg) | 0.3 | 1.89 |
| Biotin (µg) | 2.2 | 13.9 |
| Choline (mg) | 10 | 63 |
| Inositol (mg) | 5.0 | 31.5 |
| Taurine (mg) | 7.0 | 44.1 |
| Carnitine (mg) | 1.6 | 10.1 |
| Fe (mg) | 1.2 | 7.56 |
| I (µg) | 15 | 94.5 |
| Cu (mg) | 0.07 | 0.44 |
| Se (µg) | 2.0 | 12.6 |
| Zn (mg) | 0.75 | 4.72 |
| Nucleotides |  |  |
| CMP (mg) | 2.3 | 14.5 |
| UMP (mg) | 1.5 | 9.5 |

-continued

|  | per 100 kcal | per litre |
|---|---|---|
| AMP (mg) | 0.7 | 4.4 |
| GMP (mg) | 0.3 | 1.9 |
| Probiotics |  |  |
| B. lactis CNCM I-3446 | $2 \times 10^7$ cfu/g powder | |
| L. rhamnosus CGMCC 1.3724 | $2 \times 10^7$ cfu/g powder | |

This nutritional composition may be fed to an infant during a period of catch-up growth following a period of growth restriction as the sole source of nutrition from birth to the age of six months and subsequently as part of a mixed diet during the introduction of solid foods until weaning is complete at about the age of 12 months.

EXAMPLE 2

This example investigates the effect of protein type on body composition and insulin sensitivity using a rat model of semistarvation-refeeding.

Animals and Diets

All rats were obtained from Elevage Janvier (France), caged singly in a temperature-controlled room (22±1° C.) with a 12-h light/dark cycle, and maintained on a commercial chow diet (Kliba, Cossonay, Switzerland) consisting, by energy, of 24% protein, 66% carbohydrates, and 10% fat, and had free access to tap water. 6 wk old male Sprague-Dawley rats were divided into 3 groups (n=6-8) of similar mean body weight and food-restricted for a period of 2 weeks, during which they received daily a fixed-ration of chow corresponding to about 50% of their spontaneous ad libitum daily food intake. After this semistarvation phase, during which growth was essentially arrested, the animals were re-fed for 2 weeks on the test-diets shown in Table 1 below. Each group of rats received a diet with a different protein component—in the Group 1 diet the protein was bovine casein, in the Group 2 diet, the protein was bovine whey and in the Group 3 diet the protein was bovine whey in a micellar structure. All test diets were provided in isocaloric amounts (90 kcal per rat per day) which correspond to the average metabolisable energy intake of spontaneously growing male Sprague-Dawley rats in this weight range (220-350 g) under laboratory conditions. All diets were provided as a paste in plastic containers fixed to the rat cages—this form of diet delivery avoids spillage.

Determination of Body Composition

Following sacrifice by decapitation, the skull, thorax and abdominal cavity were incised and the gut cleaned of undigested food. The whole carcasses were then dried to a constant weight in an oven maintained at 70° C. and subsequently homogenized. Duplicate samples of the homogenized carcass were analyzed for fat content by the Soxhlet extraction method. Body water was obtained as the difference between final body weight and dry carcass weight, while lean body mass was determined from the difference between carcass dry weight and carcass fat.

Glucose Tolerance Test

On day 14 of re-feeding, glucose-tolerance tests were performed according to the protocol described previously (Crescenzo R, Samec S, Antic V, Rohner-Jeanrenaud F, Seydoux J, Montani J P, Dulloo A G. "A role for suppressed thermogenesis favouring catch-up fat in the pathophysiology of catch-up growth" Diabetes 52, 1090-1097 (2003)). Food was removed early in the morning (7 to 8:00 A.M.), and about 6 h later (around 13-14 h) blood was drained from the tail vein, and immediately followed by an intraperitoneal injection of glucose (2 g/kg body weight). At intervals of 30 min for the next 2h period, blood samples (about 0.5 ml) were taken from the tail vein, transferred on ice. The blood samples were then centrifuged, and the plasma frozen and stored at −20° C. for later assays of insulin (by ELISA, Crystal Chem) and glucose (using a Beckman glucose analyzer).

Statistics

All data are presented as means and standard error (SE). The data on body composition were analysed by one-factor analysis of variance, followed by post-hoc comparison tests; p values less than 0.5 were taken as the level for statistical significance of results. The data for plasma glucose and insulin during the glucose tolerance test were analyzed by 2-factor ANOVA with Diet as one factor and Time as the other factor.

TABLE 1

| DIET COMPOSITION (BY WEIGHT) | % |
|---|---|
| PROTEIN | 30-31 |
| MIX MINÉRAL AIN 93M | 4.5 |
| MIX VITAMINIQUE AIN 93VX | 1.3 |
| T-BHQ | 0.08 |
| CHOLINE BITARTRATE | 0.25 |
| CELLULOSE | 6.5 |
| SUCRE SEMOULE | 10 |
| AMIDON DE MAIS | 19.4-20.5 |
| HUILE DE MAIS | 13 |
| HUILE DE SOJA | 13.5 |

Figure 1:
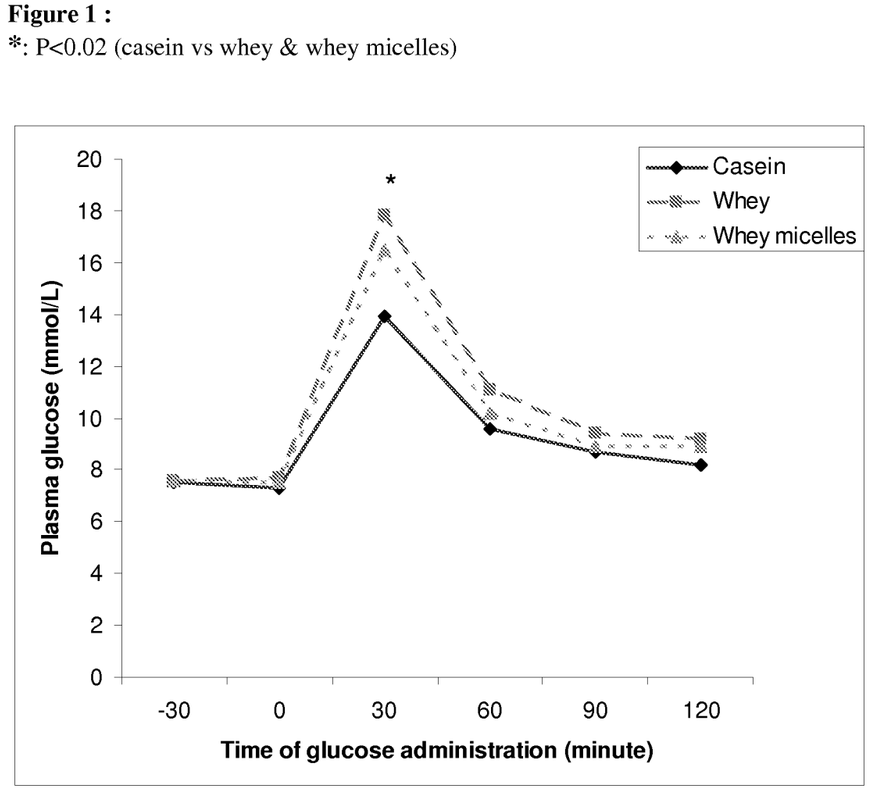
FIG. 1 shows the evolution over time of plasma glucose content in three groups of rats re-fed diets with different protein components.
Figure 2:
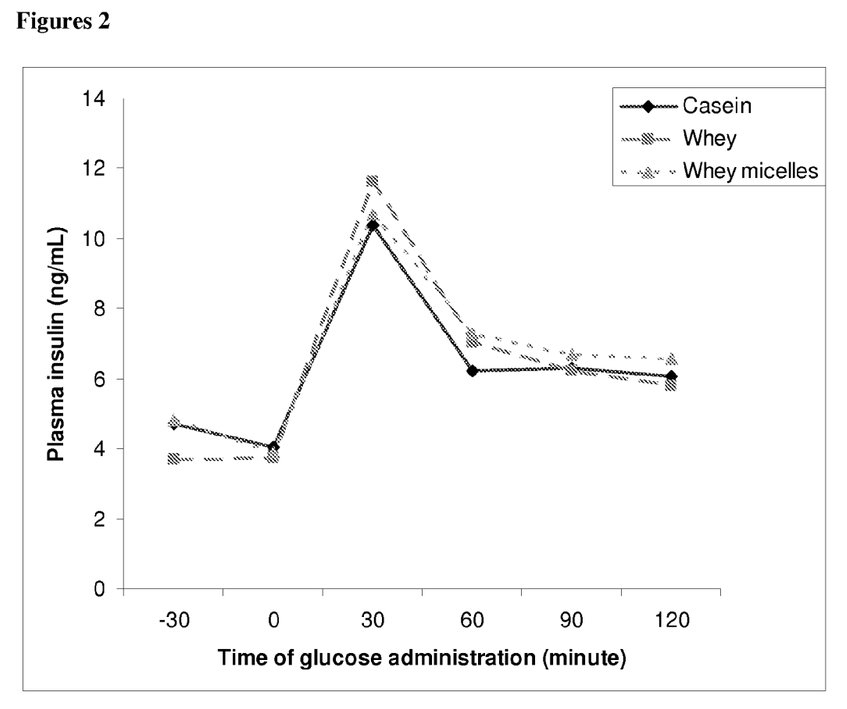
FIG. 2 shows the evolution over time of plasma insulin content in three groups of rat re-fed diets with different protein components.

No differences in body weight or body composition were observed between the three groups. Examination of the data from the glucose tolerance tests however revealed that the group re-fed on the casein diet (Group 1) showed significantly lower plasma glucose response than the groups re-fed on dietary protein derived from whey or whey micelles (FIG. 1). Furthermore, although no statistical difference was observed in plasma insulin across the three groups, Group 1 did show a lower plasma insulin profile (FIG. 2). Taken together, these data suggest that the casein diet, although without an impact on body composition, may nevertheless improve insulin sensitivity during re-feeding.

EXAMPLE 3

This example investigates the effect of protein type on growth and glucose tolerance and later basal glycaemia, and insulinaemia and insulin sensitivity (assessed by ratio of basal glucose to insulin) in a rat model of intrauterine growth restriction.

Animals and Diets 27 gestating rats and 6 virgin rats were purchased from Charles River (France) After arrival, the animals were caged individually in a room at 25° C. with 55% relative humidity and a 12 h light /dark cycle and had free access to water and a commercial chow rat diet (Kliba 3434; Provimi, CH-4303 Kaiseraugst, Switzerland). At day 10 of gestation the gestating animals were divided randomly into two groups with similar body weight. One group continued to have free access to food (non IUGR group, n=7)) and the other group was exposed to IUGR by 50% food restriction (relative to non-pregnant rats) from day 11 gestation until birth (IUGR group, n=20)

After birth, the body weight of pups was recorded within 24 hr of birth and the number of pups was limited to 8 in each litter. The pups suckled milk from their own mother until the age of 21 days.

At age 21 days, the male IUGR pups were randomized into two groups (IUGR casein and, IUGR whey, n=20/group) with similar body weights and maternal origin (same number of pups from each litter in each group). All animals (IUGR and non-IUGR groups) were caged individually and fed with their respective following diets for 4 weeks (Phase I of study).

Non IUGR group:, chow diet (Kliba 3437)
IUGR Casein: Semi-synthetic diet with casein (Table 2)
IUGR whey: Semi-synthetic diet with whey (Table 2)

TABLE 2

| PRODUITS | Casein g/100 g | Whey g/100 g |
|---|---|---|
| Cornstarch | 53 | 53 |
| Caséine | 20 | |
| Whey | | 20.3 |
| Sucrose | 10 | 10 |
| Soybean oil | 7 | 7 |
| Cellulose | 5 | 5 |
| Min. Mix AIN93G* | 3.5 | 3.5 |
| Vit. Mix AIN93 | 1.0 | 1.0 |
| L- Cystine | 0.3 | |
| Bitartr. choline | 0.25 | 0.25 |
| Tert-butylhydroquinone | 0.014 | 0.014 |
| Total (wet weight) | 100 | 100 |
| kcal/100 g diet | 365.0 | 365.00 |
| % Energy | | |
| Protein | 20 | 20 |
| CHO | 64 | 64 |
| Fat | 16 | 16 |

During follow up (Phase II: age 47-120 days) all groups received a low fat commercial diet (Kliba 3437, 10% of energy from fat).

The body weight and food intake of the animals were measured at least 2 times/week throughout study. Body composition (body fat, lean mass and body water content) was measured at 42 and 119, days using nuclear magnetic resonance (EchoMRI TM 2004, Echo Medical Systems, Houston, USA).

Glucose Tolerance Test

At age 47 days an intraperitoneal glucose tolerance test (IPGTT) was performed after 6 h of day time food deprivation (from 7.30 am to 13.30 pm). Two baseline blood samples were taken from the tail vein within 10 minutes then an intraperitoneal injection of a glucose solution at a dose of 2 g glucose/kg body weight was administered. Six further blood samples were collected from the tail vein at 15, 30, 45, 60, 90 and 120 minutes after glucose administration. Glucose in the blood samples was measured using a glucometer (Bayer, Ascensia ELITE XL, IN 46544, USA). The blood samples were centrifuged and the plasma was frozen and stored at -40° C. for subsequent insulin analysis by an ELISA method using kit from Crystal Chem. Inc (Il, USA). In addition, baseline glycaemia and insulinaemia were assessed by taking a blood sample from the tail vein at age of 119-120 days. The ratio of basal glucose to insulin ratio was calculated as an index of insulin sensitivity.

Results

Figure 3:
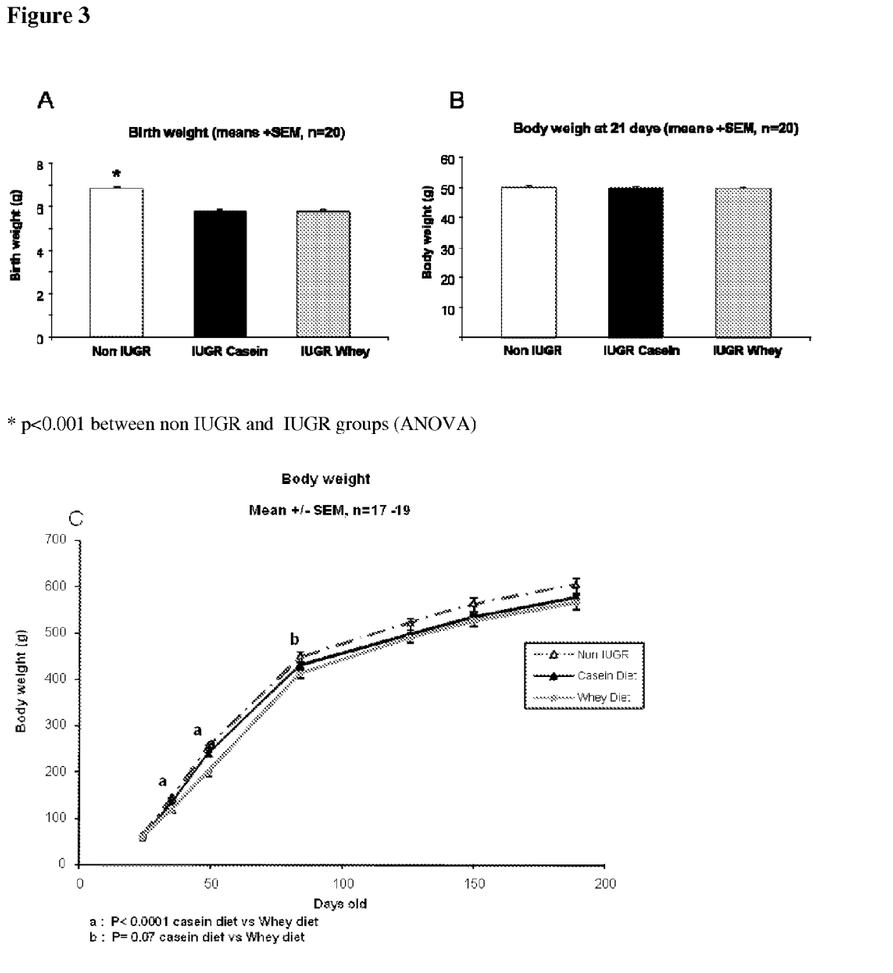
FIG. 3 shows the mean birth weight and weight at the end of the suckling period and up to age of 190 days of three groups of rat pups two groups of which were born to dams who had undergone food restriction during gestation to provoke intra-uterine growth restriction in the pups.

The body weight of IUGR casein pups was significantly higher than that of IUGR whey pups (and closer to the non IUGR control group) from age of 21 days up to the age of 90 days but not longer (FIG. 3C). The body compositions of all groups were similar during phase I & phase II.

As may be seen from FIG. 3A, the birth weight of food-restricted group was 15% lower than that of the non restricted group (p<0.001) confirming that IUGR had been successfully induced by prenatal food restriction in both casein and whey groups. All pups from IUGR dams groups showed accelerated growth or catch up growth during suckling period and the body weight of all groups was similar at the end of suckling period (FIG. 3B).

Both IUGR groups had a higher glucose response in the IPGTT (relative to non-IUGR groups) (FIG. 4) but without significant differences in insulin response at the end of diet intervention (age 42 days). Thus, as expected, both IUGR groups with rapid catch up growth had lower insulin sensitivity compared to the non-IUGR groups.

Figure 4:
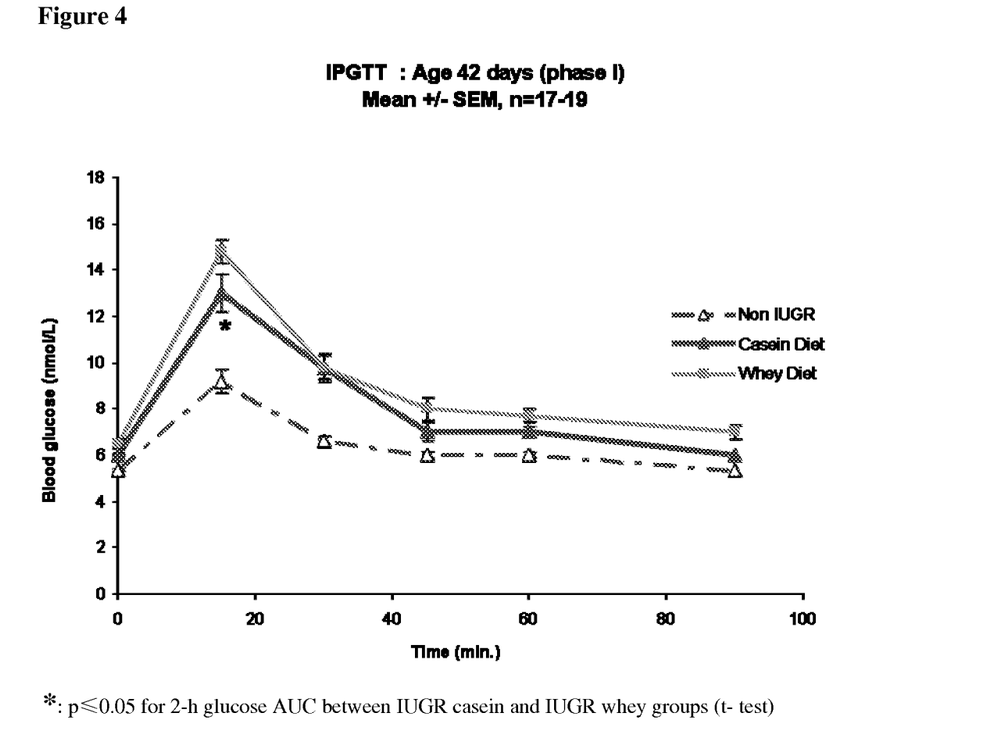
FIG. 4 shows the mean glucose responses of the three groups to an intra-peritoneal glucose tolerance test at age 42 days.
Figure 5:
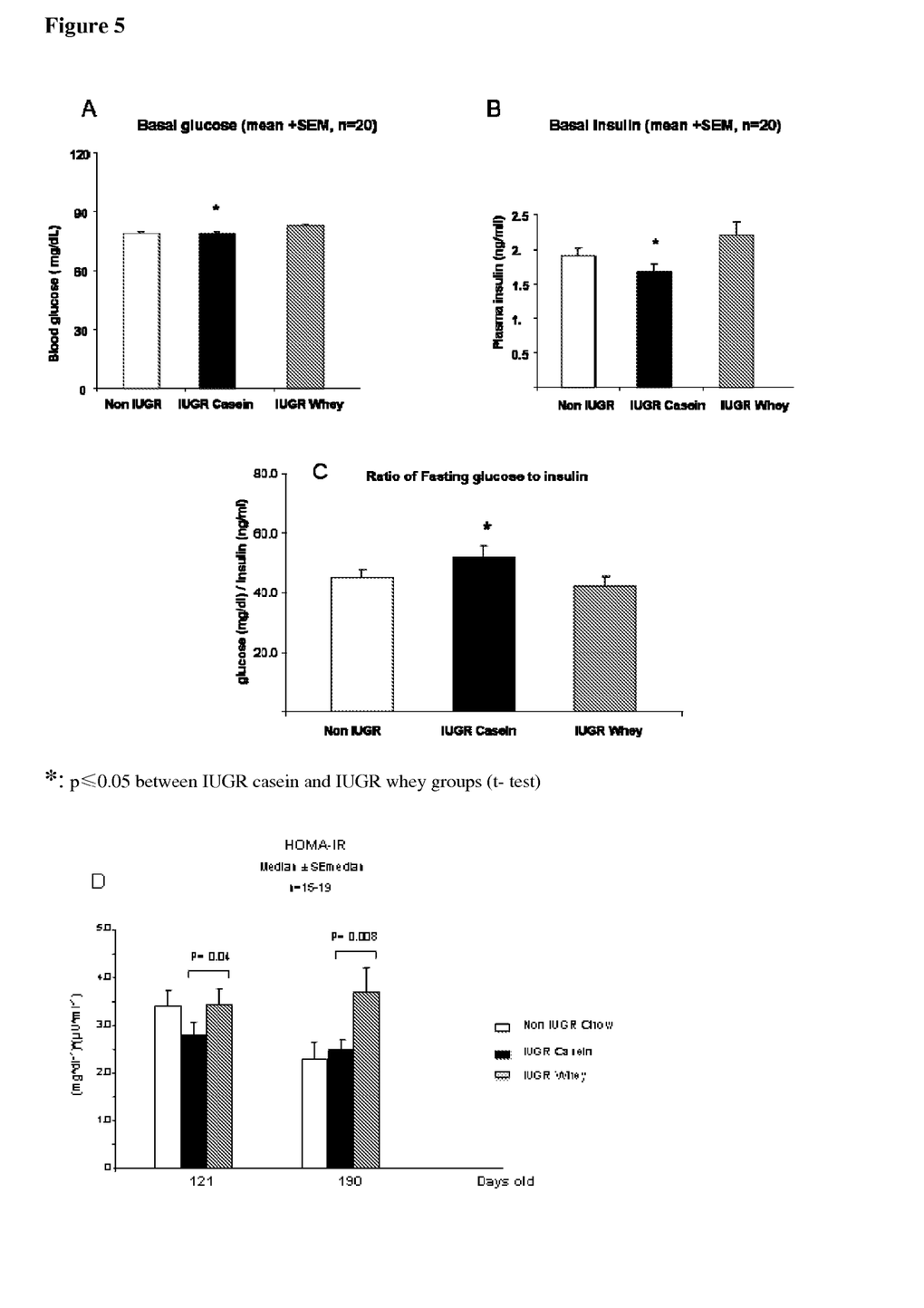
FIG. 5 shows the mean basal blood glucose, plasma insulin, ratio of basal glucose to insulin (index of insulin sensitivity), and HOMA IS (index of insulin resistance) of the three groups at age 121 days.

However, FIG. 4 also shows that the glucose response to IPGTT (2-h area under curve) was significantly lower in the group fed with the casein diet compared to that fed the whey diet (p<0.05). This beneficial effect of the casein diet on glucose tolerance was accompanied by a slight but not significant increase in insulin response (p>0.05). More importantly, FIG. 5 shows that, at the age of 121 days when all groups were being fed the same diet, the group previously fed the casein based diet had significantly lower basal blood glycaemia (FIG. 5A) and plasma insulinaemia (FIG.5B) compared to the group which had been fed the whey based diet (p<0.05 in both cases). The HOMA IR (FIG. 5D), index of insulin resistance was also significantly lower in IUGR animals which had been fed with casein diet relative to those which had been fed with the whey diet. Furthermore, the basal glucose to insulin ratio (FIG. 5C), index of insulin sensitivity, was also significantly higher in the IUGR animals which had been fed with the casein diet relative to those which have been with whey diet.

These data confirm the beneficial effect of feeding a diet based on casein protein as regards to glucose tolerance (short term benefit), later basal glycaemia and insulinaemia and insulin sensitivity during and after the period of catch up growth.

The invention claimed is:

1. A method for improving growth of an infant or young child and reducing the risk of development of insulin resistance or Type 2 diabetes of an infant or young child undergoing a period of catch-up growth following a period of intra-uterine growth restriction, during or after the period of catch-up growth, comprising the step of administering to such an infant or child a composition comprising a protein source comprising bovine casein that provides 100% by weight of the protein source, the composition administered daily during the period of catch-up growth, the protein source is between 1.6 and 2.0 g/100 kcal of the composition, and the improved growth is relative to growth from a composition comprising a protein source with a lower casein concentration.

2. The method of claim 1, wherein the infant is a pre-term infant or an infant which has been subject to intra-uterine growth retardation.

3. The method of claim 2, wherein the energy density of the composition is between 620 and 640 kcal/liter.

4. The method of claim 1, wherein the proteins are intact.

5. The method of claim 2, wherein the nutritional composition comprises lactose.

6. The method of claim 2, wherein the nutritional composition comprises a lipid source including linoleic acid (C18: 2n-6) and α-linolenic acid (C18:3n-3) such that the ratio of linoleic acid:α-linolenic acid is between 7:1 and 5:1.

7. A method for improving growth of an infant or young child and reducing the risk of development of insulin resistance or Type 2 diabetes of an infant or young child undergoing a period of catch-up growth following a period of intra-uterine growth restriction, during or after the period of catch-up growth, comprising the step of administering to such an infant or child a composition comprising a protein source comprising bovine casein that provides between 40 and 100% by weight of the protein source, the composition administered daily during the period of catch-up growth, the protein source is between 1.6 and 2.0 g/100 kcal of the composition, and the improved growth is relative to growth from a composition comprising a protein source with a lower casein concentration.

8. The method of claim 7, wherein the infant is a pre-term infant or an infant which has been subject to intra-uterine growth retardation.

9. The method of claim 7, wherein the protein source comprises both casein and whey proteins and the casein:whey ratio is from 70:30 to 30:70.

10. The method of claim 9, wherein the whey protein is sweet whey from which the caseino-glycomacropeptide has been removed and the composition comprises free phenylalanine in an amount of up to 2.2%, free isoleucine in an amount of up to 0.92%, free tryptophan in an amount of up to 0.34% and free histidine in an amount of up to 0.19%, in each as a percentage by weight of total protein content.

11. The method of claim 7, wherein the energy density of the composition is between 620 and 640 kcal/liter.

12. The method of claim 7, wherein the proteins are intact.

13. The method of claim 7, wherein the nutritional composition comprises lactose.

14. The method of claim 7, wherein the nutritional composition comprises a lipid source including linoleic acid (C18:2n-6) and α-linolenic acid (C18:3n-3) such that the ratio of linoleic acid:α-linolenic acid is between 7:1 and 5:1.

* * * * *